US007803528B1

(12) United States Patent
Chiang et al.

(10) Patent No.: US 7,803,528 B1
(45) Date of Patent: Sep. 28, 2010

(54) FLUORESCENCE ENERGY TRANSFER BY COMPETITIVE HYBRIDIZATION

(75) Inventors: Chih-Sheng Chiang, Chatsworth, CA (US); Jose F Cuan, Port Hueneme, CA (US)

(73) Assignee: Quest Diagnostics Incorporated, Wilmington, DE (US)

( * ) Notice: Subject to any disclaimer, the term of this patent is extended or adjusted under 35 U.S.C. 154(b) by 0 days.

(21) Appl. No.: 09/031,087

(22) Filed: Feb. 26, 1998

(51) Int. Cl.
*C12Q 1/68* (2006.01)
*C12P 19/34* (2006.01)
*C07H 21/04* (2006.01)
*C07H 21/00* (2006.01)

(52) U.S. Cl. ........................ 435/6; 435/91.1; 435/91.2; 536/24.3; 536/25.32

(58) Field of Classification Search ................ 435/91.2, 435/6, 91.1; 536/24.3, 25.32
See application file for complete search history.

(56) References Cited

U.S. PATENT DOCUMENTS

| | | | | | |
|---|---|---|---|---|---|
| 4,766,062 | A | * | 8/1988 | Diamond et al. | 435/6 |
| 4,965,188 | A | * | 10/1990 | Mullis et al. | 435/6 |
| 5,270,184 | A | * | 12/1993 | Walker et al. | 435/91.2 |
| 5,491,063 | A | | 2/1996 | Fisher et al. | 435/6 |
| 5,538,848 | A | | 7/1996 | Livak et al. | 435/5 |
| 5,565,322 | A | | 10/1996 | Heller | |
| 5,571,673 | A | | 11/1996 | Picone | 435/6 |
| 5,573,906 | A | | 11/1996 | Bannwarth et al. | 435/6 |
| 5,691,145 | A | | 11/1997 | Pitner et al. | 435/6 |
| 5,691,146 | A | | 11/1997 | Mayrand | 435/6 |
| 5,716,784 | A | * | 2/1998 | Di Cesare | 435/ 6 |
| 5,824,473 | A | * | 10/1998 | Meade et al. | 435/6 |
| 5,849,489 | A | * | 12/1998 | Heller | 435/6 |
| 6,103,476 | A | * | 8/2000 | Tyagi et al. | 435/6 |

FOREIGN PATENT DOCUMENTS

| | | | | |
|---|---|---|---|---|
| EP | 232 967 | A2 | | 8/1987 |
| EP | 0 461 863 | A1 | * | 12/1991 |
| EP | 0461863 | A1 | * | 12/1991 |
| EP | 0 745 690 | A | | 12/1996 |
| EP | 0861906 | A1 | | 9/1998 |
| WO | WO 96/34983 | | | 11/1996 |
| WO | WO 97/29210 | | | 8/1997 |
| WO | WO 97/32044 | | | 9/1997 |

OTHER PUBLICATIONS

Heid et al. Genome Research, 1996, vol. 6, p. 986-994.*
Larry E. Morrison—Detection of Energy Transfer and Fluorescence Quenching in Chapter 13 pp. 311- in Nonisotropic DNA Probe Techniques © 1992 by Academic Press, Inc.
Morrison et al. Solution Phase Detection of Polynucleotides Using Interacting Fluorescent Labels and Competitive Hybridization Analytical Biochem. 183, 231-244 (1989).
Mandelkern et al., Letters to the Editor: The Dimensions of DNA in Solution. J. Mol. Biol. (1981) 152: 153-161.
Cantor et al., Lighting up hybridization. Nature Biotechnology, (1996) 14:264.
Espy et al., Real-time PCR in clinical microbiology: Applications for routine laboratory testing. Clinical Microbiology Reviews, 19(1): 165-256 (2006).
Fiandaca et al., Self-reporting PNA/DNA primers for PCR analysis. Genome Research, 11: 609-613, 2001.
Harrison et al., Screening for oligonucleotide binding affinity by a convenient fluorescence competition assay. Nucleic Acids Research, 27(17): e14, i-v, 1999.
Nazarenko et al., A closed tube format for amplification and detection of DNA based on energy transfer. Nucleic Acids Research, 25(12): 2516-2521, 1997.
European Search Report for EP Application 06110485.7-2401, Apr. 10, 2006.
Notice of Opposition to a European Patent from EP Patent No. 0861906B, Mar. 12, 2006.

* cited by examiner

*Primary Examiner*—Teresa Strzelecka
*Assistant Examiner*—Joyce Tung
(74) *Attorney, Agent, or Firm*—Foley & Lardner LLP

(57) ABSTRACT

A method is provided for detecting the presence of nucleotides or monitoring nucleotide amplification. It utilizes fluorescence energy transfer by competitive hybridization. Competitive hybridization is achieved by using unequal length complementary probes which have a fluorophore on one probe and a quencher on the other. The fluorophore and quencher are juxtaposed in a manner wherein the proximity of the quencher to the fluorophore produces quenching of the fluorescence of the fluorphore.

34 Claims, 1 Drawing Sheet

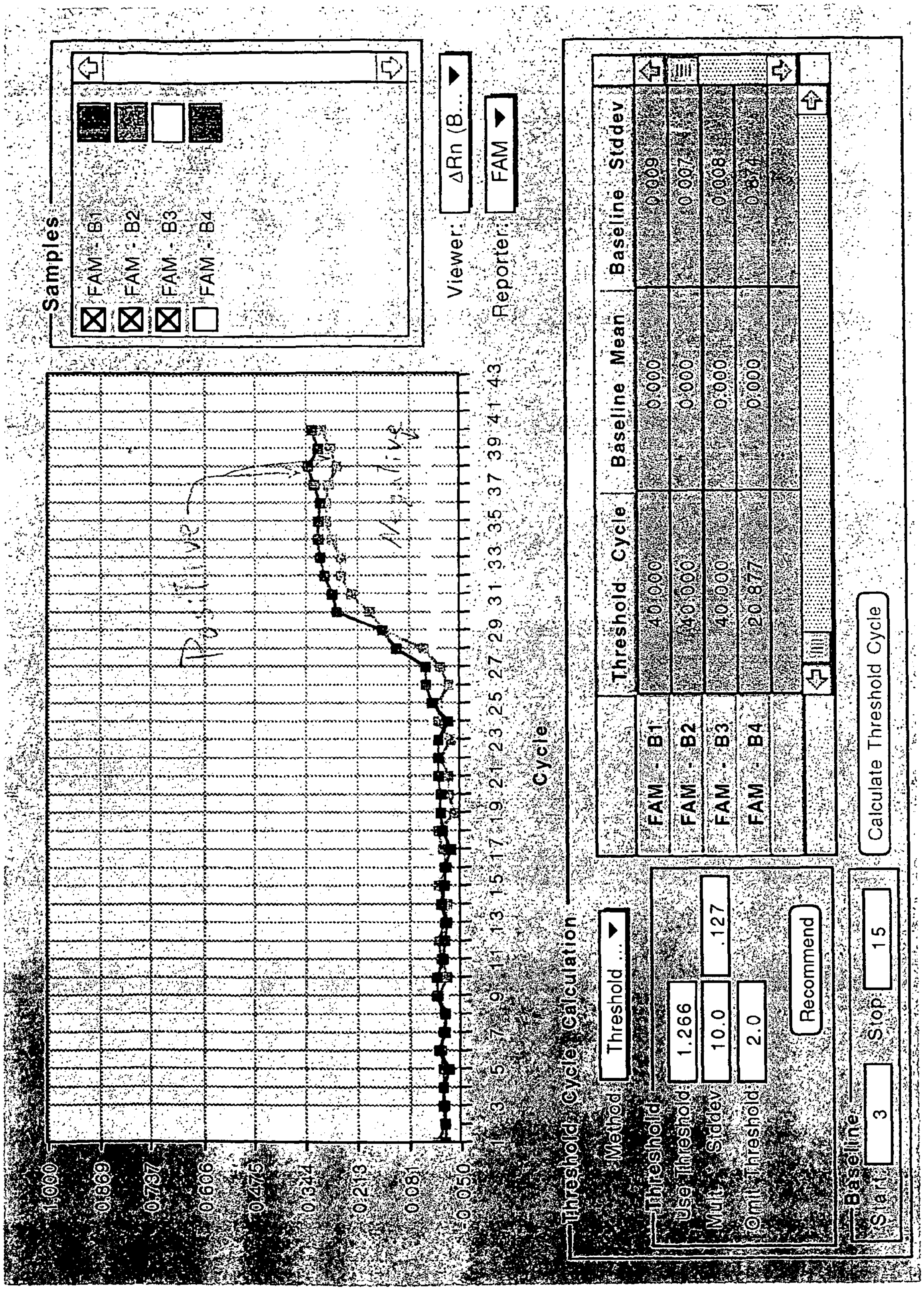
Samples
FAM - B1
FAM - B2
FAM - B3
FAM - B4
Viewer: ΔRn (B...
Reporter: FAM
1.000
0.869
0.737
0.606
0.475
0.344
0.213
0.081
-0.050
1 3 5 7 9 11 13 15 17 19 21 23 25 27 29 31 33 35 37 39 41 43
Cycle
Threshold Cycle
Baseline Mean
Baseline Stddev
FAM - B1 40.000 0.000 0.009
FAM - B2 40.000 0.000 0.007
FAM - B3 40.000 0.000 0.008
FAM - B4 20.877 0.000
Threshold Cycle Calculation
Method Threshold ...
Threshold
Use Threshold 1.266
Mult. Stddev 10.0 .127
Omit Threshold 2.0
Recommend
Baseline
Start 3
Stop 15
Calculate Threshold Cycle

SEQUENCE LISTING

<160> NUMBER OF SEQ ID NOS: 5

<210> SEQ ID NO 1
<211> LENGTH: 26

-continued

```
<212> TYPE: DNA
<213> ORGANISM: Hepatitis C virus

<400> SEQUENCE: 1

gcgttagtat gagtgtcgtg cagcct                                          26


<210> SEQ ID NO 2
<211> LENGTH: 20
<212> TYPE: DNA
<213> ORGANISM: Hepatitis C virus

<400> SEQUENCE: 2

ggtgcacggt ctacgagacc                                                 20


<210> SEQ ID NO 3
<211> LENGTH: 20
<212> TYPE: DNA
<213> ORGANISM: Hepatitis C virus

<400> SEQUENCE: 3

ccgggagagc catagtggtc                                                 20


<210> SEQ ID NO 4
<211> LENGTH: 17
<212> TYPE: DNA
<213> ORGANISM: Hepatitis C virus

<400> SEQUENCE: 4

cactatggct ctcccgg                                                    17


<210> SEQ ID NO 5
<211> LENGTH: 360
<212> TYPE: DNA
<213> ORGANISM: Hepatitis C virus

<400> SEQUENCE: 5

actcccctgt gaggaactac tgtcttcacg cagaaagcgt ctagccatgg cgttagtatg     60

agtgtcgtgc agcctccagg accccccctc ccgggagagc catagtggtc tgcggaaccg    120

gtgagtacac cggaattgcc aggacgaccg ggtcctttct tggataaacc cgctcaatgc    180

ctggagattt gggcgtgccc ccgcaagact gctagccgag tagtgttggg tcgcgaaagg    240

ccttgtggta ctgcctgata gggtgcttgc gagtgccccg ggaggtctcg tagaccgtgc    300

accatgagca cgaatcctaa acctcaaaga aaaaccaaac gtaacaccaa ccgtcgccca    360
```

FLUORESCENCE ENERGY TRANSFER BY COMPETITIVE HYBRIDIZATION

SCOPE OF THE INVENTION

This invention relates to unequal length complementary probes which have a fluorophore on one probe and a quencher on the other. The fluorophore and quencher are juxtaposed in a manner such that the proximity of the quencher to the fluorophore quenches the fluorescence of the fluorophore. These probes are useful in detecting nucleotides with sequence complemenarity. The detection capabilities reside in the competitive hybridization resulting from the use of unequal length probes, and the subsequent decrease in quenching brought about by this competitive hybridization.

AREA OF THE INVENTION

Nucleic acid amplification techniques have added to the collection of techniques by which very small quantities of a nucleotides can be enhanced to a concentration where they can be detected by some means. Several amplification techniques have become available. The most wide-spread technique is that of polymerase chain reaction, or PCR as it is now commonly called. While the amplification techniques increase the number of target nucleotide sequences available for detection, or recovery and use, a sensitive method is needed to detect the amplification product. Also, amplification technologies benefit from real-time monitoring of the amplification process. Real-time monitoring can detect non-reactive amplification runs, or detect inefficiencies in the process. Quantification of oligonucleotide burden may also be possible with real-time monitoring if such monitoring can be done without interfering with the amplification reaction.

The procedure of this invention is based on the fluorescence energy transfer between a fluorophore labeled probe and a quencher labeled probe, with sequence complementarity to each other. The probes used are of unequal length favoring the annealing of one probe to the target nucleic acid sequence over annealing to its complementary probe. In the absence of nucleic acids with sequences complementary or identical to the probe sequences (target sequence), the two probes would anneal to each other. When the two probes are annealed to each other, the proximity of the quencher to the fluorophore produces quenching of the fluorescence of the fluorophore. In the presence of nucleic acid with sequences complementary or identical to the probe sequence, some of the fluorophore labeled probe will hybridize to the nucleic acid target with the complementary sequence and be separated from the quencher and yield increased (unquenched) fluorescence. This difference in fluorescence can be used for specific detection of the presence of nucleic acids with the target sequences.

SUMMARY OF THE INVENTION

In a first aspect, this invention relates to a method for monitoring nucleic acid amplification comprising performing nucleic acid amplification on a target polynucleotide wherein the amplification is carried out by any method using a first primer and second primer of varying in length by about at least 3 base pairs and capable of hybridizing to said target polynucleotide and a first oligonucleotide probe and a second shorter oligonucleotide probe varying in length by about at least 2 base pairs; the first probe having a fluorophore; the second being complementary with the first probe and having a quencher molecule capable of quenching the fluorescence of said fluorophore, the fluorophore and quencher being attached on their respective probes at positions which results in the quencher molecule quenching the fluorescence of the fluorophore when the probes are hybridized, wherein the longer probe binds preferentially to the target polynucleotide and when preferentially bound to the target polynucleotide the fluorescence intensity of the fluorophore is greater than the fluorescence intensity of the fluorophore when hybridized to the second probe, and monitoring the fluorescence of the fluorophore, the generation of fluorescence corresponding to the occurrence of nucleic acid amplification.

It also relates to a method for detecting the presence of a target polynucleotide using the unequal length probes.

The annealed probes with fluorophore and quencher are also part of this invention.

BRIEF DESCRIPTION OF THE DRAWINGS

FIG. 1 illustrates the fluorescence signal obtained from a PCR amplification of target HCV RNA using unequal length probes where the longer probe had fluorophore on the 5' terminal carbon, the shorter probe had a quencher on the 3' terminal carbon and was prepared by deleting three base pairs from the 5' terminus of the longer probe.

DETAILED DESCRIPTION OF THE INVENTION

This invention is used in conjunction with the amplification of a target polynucleotide by any method. These amplification techniques include PCR, ligase chain reaction (LCR), gap LCR, transcription mediated amplification (TAM), nucleic acid sequence based amplifications (NASBA), and strand displacement amplification (SDA).

PCR is of greatest interest. PCR is described in many references, such as Innis et at, editors, PCR Protocols (Academic Press, New York, 1989); Sambrook et at, Molecular Cloning, Second Edition (Cold Spring Harbor Laboratory, New York, 1989); and the like. The binding site of the oligonucleotide probe is located between the PCR primers used to amplify the target polynucleotide. The PCR may be carried out using any polymerase. Because the intensity of the fluorescence signal intensifies as more replicates are made of the target polynucleotide, any polymerase which increased the number of target polynucleotides will work in this method. Preferably, PCR is carried out using a thermostable polymerase. The preferred enzyme is a Taq DNA polymerase, e.g. Amplitaq™. (Perkin-Elmer, Norwalk, Conn.), or an equivalent thermostable DNA polymerase. The annealing temperature of the PCR will be about 5 degree-10 degree C. below the melting temperatures the oligonucleotide probes employed. The polymerase Pwo has also been used with success in this invention.

The term "oligonucleotide" as used herein includes linear oligomers of natural or modified monomers or linkages, including deoxyribonucleosides, ribonucleosides, and the like, capable of specifically binding to a target polynucleotide by way of a regular pattern of monomer-to-monomer interactions, such as Watson-Crick type of base pairing, or the like. Usually monomers are linked by phosphodiester bonds or analogs thereof to form oligonucleotides ranging in size from a few monomeric units, e.g. 3-4, to several tens of monomeric units. Whenever an oligonucleotide is represented by a sequence of letters, such as "ATGCCTG," it will be understood that the nucleotides are in a 5' to 3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoranilidate, phosphoramidate, and the like. Generally, oligonucleotide probes of the invention will have a sufficient number of phosphodiester linkages adjacent to its 5' end so that the 5' to 3' exonuclease activity employed can efficiently degrade the bound probe to separate the reporter and quencher molecules.

"Perfectly matched" in reference to a duplex means that the poly- or oligonucleotide strands making up the duplex form a double stranded structure with one other such that every nucleotide in each strand undergoes Watson-Crick base pairing with a nucleotide in the other strand. The term also comprehends the pairing of nucleoside analogs, such as deoxyinosine, nucleosides with 2-aminopurine bases, and the like, that may be employed. Conversely, a "mismatch" in a duplex between a target polynucleotide and an oligonucleotide probe or primer means that a pair of nucleotides in the duplex fails to undergo Watson-Crick bonding.

Oligonucleotide probes of the invention can be synthesized by a number of approaches, e.g. Ozaki et at, Nucleic Acids Research, 20:5205-5214 (1992); Agrawal et at, Nucleic Acids Research, 18:5419-5423 (1990); or the like. The oligonucleotide probes of the invention are conveniently synthesized on an automated DNA synthesizer, e.g. an Applied Biosystems, Inc. Foster City, Calif.) model 392 or 394 DNA/RNA Synthesizer, using standard chemistries, such as phosphoramidite chemistry, e.g. disclosed in the following references: Beaucage and Iyer, *Tetrahedron,* 48:2223-2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the hybridization efficiencies of the resulting oligonucleotides and/or cleavage efficiency of the exonuclease employed are not adversely affected. Preferably, the oligonucleotide probe is in the range of 15-60 nucleotides in length. More preferably, the oligonucleotide probe is in the range of 18-30 nucleotides in length. The precise sequence and length of an oligonucleotide probe of the invention depends in part on the nature of the target polynucleotide to which it binds. The binding location and length may be varied to achieve appropriate annealing and melting properties for a particular embodiment. Preferably, the 3' terminal nucleotide of the oligonucleotide probe is blocked or rendered incapable of extension by a nucleic acid polymerase. Such blocking is conveniently carried out by the attachment of a reporter or quencher molecule to the terminal 3' carbon of the oligonucleotide probe by a linking moiety. Preferably, reporter molecules are fluorescent organic dyes derivatized for attachment to the terminal 3' carbon or terminal 5' carbon of the probe via a linking moiety. Preferably, quencher molecules are also organic dyes, which may or may not be fluorescent, depending on the embodiment of the invention. For example, in a preferred embodiment of the invention, the quencher molecule is fluorescent. Generally, whether the quencher molecule is fluorescent or simply releases the transferred energy from the reporter by non-radiative decay, the absorption band of the quencher should substantially overlap the fluorescent emission band of the reporter molecule. Non-fluorescent quencher molecules that absorb energy from excited reporter molecules, but which do not release the energy radiatively, are referred to herein as chromogenic molecules. There is a great deal of practical guidance available in the literature for selecting appropriate reporter-quencher pairs for particular probes, as exemplified by the following references: Clegg "Fluorescence resonance energy transfer and nucleic acids," Methods of Enzymology, 211: 353-389 (1992), Wu et al; "Resonance energy transfer: methods and applications," Anal. Biochem. 218: 1-13 (1994).; Pesce et at, editors, Fluorescence Spectroscopy (Marcel Dekker, New York, 1971); White et at, Fluorescence Analysis: A Practical Approach (Marcel Dekker, New York, 1970); and the like. The literature also includes references providing exhaustive lists of fluorescent and chromogenic molecules and their relevant optical properties for choosing reporter-quencher pairs, e.g. Berlman, Handbook of Fluorescence Sprectra of Aromatic Molecules, 2nd Edition (Academic Press, New York, 1971); Griffiths, Colour and Consitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); and the like. Further, there is extensive guidance in the literature for derivatizing reporter and quencher molecules for covalent attachment via common reactive groups that can be added to an oligonucleotide, as exemplified by the following references: Haugland (cited above); Ullman et al, U.S. Pat. No. 3,996,345; Khanna et al, U.S. Pat. No. 4,351,760; and the like.

Exemplary reporter-quencher pairs may be selected from xanthene, dyes, including fluoresceins, and rhodamine dyes. Many suitable forms of these compounds are widely available commercially with substituents on their phenyl moieties which can be used as the site for bonding or as the bonding functionality for attachment to an oligonucleotide. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like. Preferably, reporter and quencher molecules are selected from fluorescein and rhodamine dyes. These dyes and appropriate linking methodologies for attachment to oligonucleotides are described in many references, e.g. Khanna et al (cited above); Marshall, Histochemical J., 7:299-303 (1975); Mechnen et at, U.S. Pat. No. 5,188,934; Menchen et al, European pat. No. application 87310256.0; and Bergot et al, International application PCT/US90/05565. The latter four documents are hereby incorporated by reference.

There are many linking moieties and methodologies for attaching reporter or quencher molecules to the 5' or 3' termini of oligonucleotides, as exemplified by the following references: Eckstein, editor, Oligonucleotides and Analogues: A Practical Approach (IRL Press, Oxford, 1991); Zuckerman et al, Nucleic Acids Research, 15: 5305-5321 (1987)(3' thiol group on oligonucleotide); Sharma et al, Nucleic Acids Research, 19:3019 (1991)(3' sulfhydryl); Giusti et al, PCR Methods and Applications, 2:223-227 (1993) and Fung et al, U.S. Pat. No. 4,757,141 (5' phosphoamino group via Aminolink™. II available from Applied Biosystems, Foster City, Calif.); Stabinsky, U.S. Pat. No. 4,739,044 (3' aminoalkylphosphoryl group); Agrawal et al, *Tetrahedron* Letters, 31:1543-1546 (1990)(attachment via phosphoramidate linkages); Sproat et al, Nucleic Acids Research, 15:4837 (1987) (5' mercapto group); Nelson et al, Nucleic Acids Research, 17:7187-7194 (1989)(3' amino group); and the like. Preferably, commercially available linking moieties are employed that can be attached to an oligonucleotide during synthesis, e.g. available from Clontech Laboratories (Palo Alto, Calif.).

Rhodamine and fluorescein dyes are also conveniently attached to the 5' hydroxyl of an oligonucleotide at the conclusion of solid phase synthesis by way of dyes derivatized with a phosphoramidite moiety, e.g. Woo et al, U.S. Pat. No. 5,231,191; and Hobbs, Jr. U.S. Pat. No. 4,997,928.

The selection of primers and probes used in this invention is at the choice of the practitioner. This invention places no unique requirements or restrictions on primer or probe choice. Such choices are within the skill of the art.

The probes can be of any length, so long as that length allows one to practice the invention. As a baseline the longer probe must have at least 3 base pairs; as a practical matter the longer probe will be comprised of more than 3 base pairs. However, there is no upper limit occasioned by the use of FETCH. The length of the longer probe is not dictated by the application of FETCH as it will work with any length of probe, over and above the basic requirement of being at least 3 base pairs long. As a practical matter the longer probe will have a length which insures that it hybridizes uniquely with the target polynucleotide and the shorter probe. The shorter probe will be at least 2 fewer base pairs than that of the longer probe. This is the basic standard for creating the shorter probe. It has been found that a good fit as regards the difference in length between the probes can be arrived at by calculating the dissociation temperature of the annealed probes. As a general rule the dissociation temperature of the primers needs to be higher than about 55 degrees C. and lower than 90 degrees A convenient means for doing this calculation is to use the software called Gene Runner (Hastings Software, Inc.), for example version 3.04.

The shorter probe may be prepared as a 5' truncate of the longer probe. Or it may be a 3' truncate. A third option is to create the shorter probe by truncating both the 5' and the 3' end of the longer probe. Any one of these three forms of the shorter probe will work. While two or more truncated forms could be used, it is simplest to use just one form, preferably the 5' truncate form.

The fluorophore and the quencher can be located on any combination of base pairs so long as the fluorescence of the fluorophore is effectively quenched by the quencher when the two probes are hybridized. The simplest approach is to put the fluorophore on the 5' terminal nucleotide of the longer probe and the quencher on the 3' terminal nucleotide of the shorter probe. This approach can optimizes the quencher molecules affect on the fluorescence of the fluorophore. Preferably, fluorphore and quencher molecules are attached to the terminal 5' carbon and terminal 3' carbon of the probe by way of 5' and 3' linking moieties. However it has been demonstrated that, with at least a number of the fluorophores useful herein, that the fluorophore and the quencher can be situated remotely and still be operative. See for example U.S. Pat. No. 5,538,848 which discloses that a fluorophore and quencher may be separated by several nucleotides. That patent discloses work where a fluorophore and quencher are separated by at least 15 nucleotides, or more, and allegedly demonstrate utility. Likewise herein the fluorophore and quencher are permitted to be separated by numerous nucleotides, so long as that separation does not materially reduce the ability of the quencher to affect the signal of the fluorophore when the two probes are hybridized. Of course the fluorophore and/or quencher could be bonded to a nucleotide in the interior of the probes. But for reasons of ease of synthesis and for optimizing hybridization of probe to target and probe to probe, it is preferable to put the fluorophore and quencher on the 5' and 3' terminal ends of the probes, as noted above. In fact the fluorophore and quencher both be on the 5' or 3' terminal nucleotides of their respective oligonucleotides, and the assay will be functional. An alternative arrangement would be to put the fluorophore on the shorter probe and the quencher on the longer probe. Again in this arrangement the longer probe would preferentially bind to the target and thus be separated sufficiently from the probe with the fluorophore so as not to effectively quench its fluorescence. The preferred construct, however, is to have the fluorophore on the longer probe.

The following examples are given to illustrate the invention and are not intended nor should they be read to limit the scope of the invention as claimed in any fashion.

EXAMPLES

General Description

The use of fluorescence energy transfer by competitive hybridization (FETCH) was developed as an assay for the detection by PCR of hepatitis C virus (HCV) in human specimens. The forward probe, the longer probe, had a 6-FAM dye (carboxyfluoroscein) at the 5' position and a phosphate group at the 3' position (to prevent extension during PCR). The reverse probe, the shorter probe, had a TAMRA dye (N,N,N', N' tetramethyl-6-carboxyrhodamine) at the 3' position (no 3' OH thus no extension possible during PCR). FAM, a commonly used fluorescent dye, was used as the fluorophore. TAMRA, a fluorescent dye with absorption band overlapping the emission band of FAM, was used as the quencher in this application

Example 1

Selection of Primers and Probes

HCV polynucleotide sequences were identified from the literature. In order to have an assay which could catch all known HCV strains, two primers and two probes were selected which had polynucleotide sequences common to all reported strain RNA sequences. The primers were selected so that they would anneal to all the known HCV strains and possess satisfactory characteristics such as similar dissociation temperature, no extensive 3' complementarity to each other, etc. The ones chosen flank a 254 by segment of the 5' non-coding region of HCV from nucleotide number 3290 to 3543 (SEQ ID NO.: 5) as described in the literature. The HCV sequence data relied on, the primers, and the selected probes are identified in the following Tables I-III (attached).

The sequence in Table I is indicated as SEQ ID NO. 5. The HCV oligo in Table II is indicated as SEQ ID NO. 1. The HCVR2 oligo in Table II is indicated as SEQ ID NO. 2. Probe C1 in Table III is indicated as SEQ ID NO. 3. Probe C2 in Table III is indicated as SEQ ID NO. 4.

TABLE I

| Oligo | Forward Primer Sequence | Bases | MW | Label |
|---|---|---|---|---|
| HCV | 5'-GCGTTAGTATGAGTGTCGTGCA GCCT-3' (SEQ. ID. NO.: 1) | 26 | 8008 | None |
| HCVR2 | 5'-GGTGCACGGTCTACGAGACC-3' (SEQ. ID. NO.: 2) | 20 | 6124 | None |

TABLE II

| | |
|---|---|
| Probe C1 | 5'-FAM-CCGGGAGAGCCATAGTGGTC-$PO_4$ (SEQ. ID NO.: 3) |
| Probe C2 | 5'-TAMRA-GGCCCTCTCGGTATCAC (SEQ. ID. NO.: 4) |

The unconventional presentation of the sequence of C2 (from 3' to 5') is to aid the visualization of its complementarity to C1.

TABLE III

| | BASES | MW | LABEL |
|---|---|---|---|
| Probe C1 | 20 | 6914 | 6-FAM |
| Probe C2 | 17 | 6065 | TAMRA |

Molecular weights calculated by Gene Runner version 3.04 (Hasting Software, Inc.).

Example 2

Synthesis of Probes

Two probes were custom-synthesized at TriLink Biotechnologies, Inc. (11585 Sorrento Valley Rd., Suite 105, San Diego, Calif. 92121) They were prepared as follows:

Step 1. Synthesis of Oligonucleotide

The oligonucleotide was prepared on a support that will yield a 3' phosphate group upon deprotection (Glen Research Catalog No. 20-2913).

Step 2. Addition of 6-FAM

The support bound oligonucleotide was then reacted with 15 eqs. of 6-FAM amidite (Glen Research Catalog No. 10-5901) manually to ensure high efficiency.

Step 3. Deprotection of Oligonucleotide

The FAM labeled oligo was deprotected for 36 hours at room temperature with fresh conc. ammonium hydroxide. After deprotection the reagent was decanted, the beads rinsed, and the combined solutions dried.

Step 4. Purification

The FAM labeled oligonucleotide was purified using reverse phase HPLC. The FAM was only on full length material, and was a useful lipophilic handle allowing good separation. After purification, the compound was dried down in preparation for precipitation. The compound was precipitated from 0.3 M NaOAc using EtOH. The product was recovered by high speed centrifugation and washed twice with EtOH.

Step 5. Final Analysis

The dried product was resuspended in water, quantitated, and analyzed by HPLC for purity. The compound was then dried again in preparation for delivery.

Example 3

Detection of HCV RNA by Reverse Transcriptase-PCR Using FETCH

The assay was carried out as a one-step reverse transcription and polymerase chain reaction. HCV RNA was isolated and purified from human serum or plasma. The serum or plasma sample was lysed under highly denaturing conditions to inactivate RNAases and to insure isolation of intact RNA. The RNA was precipitated with Fri ethanol and transferred to a QIAmp spin column (Qiagen, Chatsworth, Calif.) that binds RNA. The column was then washed and RNA eluted with water. The purified RNA template (10 μL) was mixed with HCV master mix (see Table V) (40 μL) and then reverse transcribed to DNA, amplified by PCR and detected in the same tube in the Perkin Elmer 7700 sequence analyzer as per Table VI. During PCR, some of the FAM labeled probe and some of the TAMRA labeled probe annealed to the PCR product thus reducing the quenching of FAM fluorescence and allowed increased fluorescence to be detected. The fluorescence of FAM increase with increasing number of cycles of thermocycling, corresponding with increases in amount of PCR product, as illustrated in FIG. 1.

TABLE V

Typical HCV Master Mix

| Reagents | 1 Tube μL | Final conc. (40 μL) |
|---|---|---|
| Water RNase Free | 26.8 | — |
| 10X TaqMan ™ Buffer | 5 | 1X |
| $MgCl_2$ (25 mM) | 5 | 2.5 mM |
| dNTP, (25 mM each) | 0.6 | 300 μM |
| Primer HCVC1 (100 μM) | 0.25 | 500 nM |
| Primer HCVC2 (100 μM) | 0.25 | 500 nM |
| Probe C1 (25 μM) | 0.2 | 100 nM |
| Probe C2 (25 μM) | 0.2 | 100 nM |
| RNase Inhibitor (20 U/μL) | 0.5 | 10 U |
| MU/V RT (50 U/μL) | 0.5 | 25 U |
| Amplitaq Gold (5 U/μL) | 0.5 | 2.5 U |

TaqMan is the trademark of Roch Molecular Systems, Inc.

TABLE VI

| Cycle | Temperature | Time | Repeat | Ramp Time | Auto Increment |
|---|---|---|---|---|---|
| Hold | 48 degrees C. | 60:00 | | Auto | |
| Hold | 95 degrees C. | 10:00 | | Auto | |
| Cycle | 93 degrees C. | 0:15 | 40 | Auto | |
| | 57 degrees C. | 0.30 | | | |
| | 72 degrees C. | 0.30 | | | |

What is claimed is:

1. A method for real-time monitoring of nucleic acid amplification comprising:

amplifying a target nucleic acid and monitoring said target nucleic acid during said amplification using a first oligonucleotide probe and a second oligonucleotide probe, said first probe;

i) is capable of hybridizing to said target nucleic acid;

ii) comprises a fluorophore; and iii) is not equal in length to said second probe;

said second probe;

i) is capable of hybridizing to said first probe; and ii) has a quencher molecule which quenches said first probe fluorophore when said first and second probes are hybridized to each other; and detecting fluorescence of said first probe fluorophore in real-time to monitor amplification, wherein an increase in fluorescence correlates with amplification.

2. The method of claim 1 wherein the amplification is carried out using a thermostable nucleic acid polymerase.

3. The method of claim 1 wherein the fluorophore on the first probe and the quencher molecule on the second probe are on complementary base pairs.

4. The method of claim 1 wherein the fluorophore and quencher molecules are within about 1 to 3 hybridized base pairs of each other.

5. The method of claim 1 wherein the fluorophore and quencher molecules are within 3 or more hybridized base pairs of each other.

6. The method of claim 1 wherein the fluorophore is on the 5' terminal nucleotide of the first probe and the quencher is on the 3' terminal nucleotide of the second probe.

7. The method of claim 1 wherein the fluorophore is on the 3' terminal nucleotide of the first probe and the quencher is on the 5' terminal nucleotide of the second probe.

8. The method of claim 1 wherein the second probe is shorter than the first probe.

9. The method of claim 8 wherein the second probe is at least three nucleotides shorter than the first probe.

10. The method of claim 1 wherein the first and second probes have a dissociation temperature difference of 2 degrees or more.

11. The method of claim 1 wherein the first probe has the sequence of SEQ ID NO. 3.

12. The method of claim 1 wherein the first probe has the sequence of SEQ ID NO. 4.

13. The method of claim 1 wherein the amplification method is the polymerase chain reaction and wherein a primer for use in the polymerase chain reaction has the sequence of SEQ ID NO. 1.

14. The method of claim 1 wherein the amplification method is the polymerase chain reaction and wherein a primer for use in the polymerase chain reaction has the sequence of SEQ ID NO. 2.

15. The method of claim 1 wherein the target nucleic acid comprises the hepatitis C virus genome or segment thereof.

16. The method of claim 1 wherein the method of amplification is selected from the group consisting of polymerase chain reaction, ligase chain reaction, gap ligase chain reaction, transcription mediated amplification, nucleic acid sequence based amplification and strand displacement amplification.

17. The method of claim 1 wherein the amplification method includes the use of a primer pair that flanks the first and second probe.

18. The method of claim 1 wherein the longer probe binds preferentially to the target polynucleotide and when preferentially bound to the target polynucleotide the fluorescence intensity of the fluorophore is greater than the fluorescence intensity of the fluorophore when hybridized to the second probe.

19. A method for monitoring nucleic acid amplification comprising:

(i) amplifying a target nucleic acid in a cycling amplification reaction in the presence of a first probe and a second probe;

said first probe;

i) is capable of hybridizing to said target nucleic acid;

ii) comprises a fluorophore; and iii) is not equal in length to said second probe;

said second probe;

i) is capable of hybridizing to said first probe; and ii) has a quencher molecule which quenches said first probe fluorophore when said first and second probes are hybridized to each other; and (ii) assessing the amount of amplified target nucleic acid produced by said amplification reaction by detecting the amount of fluorescence of said first probe fluorophore during a plurality of cycles of said amplification reaction, wherein the amount of fluorescence correlates with the amount of amplified target nucleic acid.

20. The method of claim 19 wherein the fluorophore on the first probe and the quencher molecule on the second probe are on complementary base pairs.

21. The method of claim 19 wherein the fluorophore and quencher molecules are within about 1 to 3 hybridized base pairs of each other.

22. The method of claim 19 wherein the fluorophore is on the 5' terminal nucleotide of the first probe and the quencher is on the 3' terminal nucleotide of the second probe.

23. The method of claim 19 wherein the fluorophore is on the 3' terminal nucleotide of the first probe and the quencher is on the 5' terminal nucleotide of the second probe.

24. The method of claim 19 wherein the second probe is shorter than the first probe.

25. The method of claim 24 wherein the second probe is at least three nucleotides shorter than the first probe.

26. The method of claim 19 wherein the first and second probes have a dissociation temperature difference of 2 degrees or more.

27. The method of claim 19 wherein the first probe has the sequence of SEQ ID NO. 3.

28. The method of claim 19 wherein the first probe has the sequence of SEQ ID NO. 4.

29. The method of claim 19 wherein the amplification reaction is the polymerase chain reaction and wherein a primer for use in the polymerase chain reaction has the sequence of SEQ ID NO. 1.

30. The method of claim 19 wherein the amplification reaction is the polymerase chain reaction and wherein a primer for use in the polymerase chain reaction has the sequence of SEQ ID NO. 2.

31. The method of claim 19 wherein the target nucleic acid comprises at least a segment of the hepatitis C virus genome.

32. The method of claim 19 wherein the method of amplification is selected from the group consisting of polymerase chain reaction, ligase chain reaction, gap ligase chain reaction, transcription mediated amplification, nucleic acid sequence based amplification and strand displacement amplification.

33. The method of claim 19 wherein the amplification reaction includes the use of a primer pair that flanks the first and second probe.

34. The method of claim 19 wherein the fluorescence of said first probe fluorophore is detected during every cycle of said amplification reaction.

* * * * *

UNITED STATES PATENT AND TRADEMARK OFFICE

CERTIFICATE OF CORRECTION

PATENT NO. : 7,803,528 B1
APPLICATION NO. : 09/031087
DATED : September 28, 2010
INVENTOR(S) : Chih-Sheng Chiang et al.

It is certified that error appears in the above-identified patent and that said Letters Patent is hereby corrected as shown below:

In Column 2, line 32, replace "amplifications" with --amplification--

In Column 5, line 29, replace "90 degrees" with --90 degrees C.--

Signed and Sealed this
Fourth Day of January, 2011

David J. Kappos
*Director of the United States Patent and Trademark Office*

UNITED STATES PATENT AND TRADEMARK OFFICE

CERTIFICATE OF CORRECTION

PATENT NO. : 7,803,528 B1
APPLICATION NO. : 09/031087
DATED : September 28, 2010
INVENTOR(S) : Chih-Sheng Chiang and Jose F. Cuan It is certified that error appears in the above-identified patent and that said Letters Patent is hereby corrected as shown below:

On the title page:
Item (63) – add priority "Provisional application No. 60/039,583 filed February 28, 1997"

Signed and Sealed this
First Day of February, 2011

David J. Kappos

David J. Kappos
*Director of the United States Patent and Trademark Office*